United States Patent [19]

Tuffel

[11] Patent Number: 4,938,221
[45] Date of Patent: Jul. 3, 1990

[54] HEMORRHOID INFLAMMATION REDUCING DEVICE

[76] Inventor: Judith S. Tuffel, 97 Cedarhurst Ave., Cedarhurst, N.Y. 11516

[21] Appl. No.: 317,917

[22] Filed: Mar. 2, 1989

Related U.S. Application Data

[63] Continuation-in-part of Ser. No. 179,878, Apr. 11, 1988, abandoned.

[51] Int. Cl.⁵ .............................................. A61F 7/12
[52] U.S. Cl. .................................. 128/401; 128/403; 606/197
[58] Field of Search ............... 128/401, 403, 343, 341, 128/344; 383/371, 372, 401; 606/192–196, 197

[56] References Cited

U.S. PATENT DOCUMENTS

| | | | |
|---|---|---|---|
| 64,283 | 8/1867 | Coates | 383/901 |
| 2,949,914 | 8/1960 | Waldrum | 383/901 |
| 3,939,842 | 2/1976 | Harris | 128/401 |
| 4,696,302 | 9/1987 | Clark | 128/401 |

FOREIGN PATENT DOCUMENTS

| | | | |
|---|---|---|---|
| 274558 | 6/1988 | European Pat. Off. | 128/401 |
| 2416881 | 3/1976 | Fed. Rep. of Germany | 128/901 |
| 838195 | 7/1958 | United Kingdom | 128/403 |

Primary Examiner—Edward M. Coven
Assistant Examiner—Mark S. Graham
Attorney, Agent, or Firm—Michael I. Kroll

[57] ABSTRACT

A hemorrhoid inflammation reducing device is disclosed. The device has a hollow flexible housing that is shaped to be inserted into and removed from the anus of the rectum of a person having internal/external hemorrhoids. The housing has an enlarged head portion to fit into the rectum, a reduced neck portion that extends from the head portion so that the neck portion can bear against the internal/external hemorrhoids, and an oversized body portion which extends from the neck portion so that the body portion can stick out from the anus allowing the person to grip the body portion for insertion into and removal from the anus of the rectum. A coolant is disposed within the housing for shrinking the internal/external hemorrhoids. A closure is provided for sealing the coolant within the housing after the coolant is placed within the housing. The closure has a pair of handle-like extensions and an aperture formed in the distal end of the body portion opposite the neck portion of the housing. The extensions are tied together sealing the coolant in the housing. The extensions are initially untied to allow the coolant to be initially filled through the aperture contained in the housing when first using the device.

4 Claims, 2 Drawing Sheets

HEMORRHOID INFLAMMATION REDUCING DEVICE

CROSS REFERENCE

This application is a continuation-in-part application of co-pending application Ser. No. 179,878 filed April 11, 1988, abandoned.

BACKGROUND OF THE INVENTION

1. Field of the Invention

The present invention relates to a treatment for hemorrhoids.

More particularly, the present invention relates to a hemorrhoid inflammation reducing device.

2. Description of the Prior Art

Hemorrhoids are simply varicose veins in the anal canal. They may come and go and almost everyone has them at one time or another. They are very common in pregnancy and occur in two locations.

Those occurring above the internal sphincter are called internal hemorrhoids and those appearing outside the external sphincter are called external hemorrhoids.

Hemorrhoids cause itching, bleeding and pain. Internal hemorrhoids prolapse frequently through the sphincter and cause considerable discomfort. If the blood within them clots and becomes infected, they become painful and the risk of a thrombosis becomes present.

The primary complications of hemorrhoids are bleeding, strangulation, and thrombosis. Trauma to the vein during defecation can cause enough bleeding to produced an iron deficiency anemia. Blood oozes or may even spurt out following a bowel movement.

Thrombosis, or clotting of the blood within the hemorrhoid, can occur at any time and is manifested by intense pain.

Prolapsed hemorrhoids may come out during defecation and spontaneously return. Prolapsed hemorrhoids may have to be returned by the patient or they may remain prolapsed.

A strangulated hemorrhoid is a prolapsed hemorrhoid in which the blood supply is cut off by the anal sphincter. The blood within the prolapsed hemorrhoid becomes clotted and thrombosis occurs which is a very painful condition that brings extreme edema and inflammation.

The treatment methods range from warm baths through ointments and suppositories to surgery or injection chemotherapy to control the bleeding and to eliminate the varicose veins. Often several methods are combined to address various aspects of the disease.

Three treatments are commonly used for the treatment of hemorrhoids a color, they are medical management, surgical excision, or laser surgery of the dilated veins and injection of a sclerosing substance into the tissues at the base of the vein. The injection of the sclerosing substance may be only temporarily effective.

Medical therapy, used only for small hemorrhoids with mild symptoms, includes reducing pressure by treating the constipation and thus keeping the stools soft. Pain is relieved with sitz baths, application of heat, and astringent lotions, such as witch hazel. A recumbent position may be needed if the hemorrhoid is prolapsed or thrombosed.

The surgical excision is done by digital dilation of the rectal sphincter and removal of the hemorrhoids by the use of a clamp and cautery or by ligation and excision. After completion of the operation procedures, a small tube, often covered with petrolatum gauze, is inserted through the sphincter to permit the escape of flatus and also of blood.

Instead of the tube, some surgeons place pieces of Gelfoam or Oxycel gauze over the anal wounds. Dressings in such cases are held in place by a T-binder. The area is either left open to heal by granulation or sutured very painfully for the patient but has a high rate of success, whereas the sutured method, while far less painful, is more likely to cause infection and fails to heal well. The surgical excision and new laser surgery on a patient is usually repeated over and over again on a regular basis, which can become incovenient.

Hemorrhoids have plagued humans from time immemorial, particularly adult humans. Hemorrhoids are a livid and painful swelling formed by vein dilation in the anal cavity or rectum. Many treatments have been deviced over the years, including chemical, thermal, electrical and surgical. Some involving elaborate treatment procedures and others somewhat drastic, and some of those already mentioned having possible damaging side effects. Many of the prior art techniques require administration by trained technicians or, in some cases, even physicians.

As long ago as 1869 Schevenell et al. in U.S. Pat. No. 77,539 proposed an instrument for treating piles or hemorrhoids involving a tapered hollow electrode of different metals to provide galvanic action when brought into contact with the body fluids. This was claimed to reduce the rectal inflammation. The electrode was inserted into the rectal cavity and held in place for several hours in order to achieve the asserted beneficial treatment.

Another unsuccessful attempt was proposed by Cowie in U.S. Pat. No. 969,134 dated August 30, 1910 who suggested the use of a hollow device, presumably of metal, having a removable screw cap so that crushed ice or other freezing, cooling, or heating medium could be employed. The device of Cowie, albeit some forty or more years after Schevenell et al., did not advance the technology, but rather had the same drawbacks and deficiencies as the proposal of Schevenell et al.

One approach to the treatment was to relieve the pain and to diminish the swelling by cooling the hemorrhoidal tissue. For instance, Cowie in U.S. Pat. No. 969,134 suggested the use of hollow inserts filled with crushed ice or other cooling medium, which was refilled for every use.

More recently, Harris in U.S. Pat. No. 3,969,842 suggested a plastic rectal insert containing an encapsulated freezable liquid, preferrably water, and being equipped with a bulbous collapsible end.

Suppositories cannot be used for the cooling effect because of their shape. The pressure of the sphincter squeezes them immediately from the rectal canal into the botton of the colon. This holds true even for hydrogel suppositories, as described by Byrne and Aylott in U.S. Pat. No. 4,292,300, which could have otherwise sufficient heat capacity due to the relatively high water content.

SUMMARY OF THE INVENTION

Accordingly, it is an object of the present invention to provide a hemorrhoid reducing device that will overcome the shortcomings of the prior art devices.

More particularly, the present invention applies a cold application to the anal canal to reduce the swelling of the internal and the external hemorrhoids so as to eliminate unnecessary repetitive surgery to the area.

The present invention is deformably shaped to hold ice or frozen gel within itself and due to its deformability can be inserted within and removed from the anal canal for treatment without any major pain.

The present invention is safe, simple and easy to use, and is economical in cost to manufacture, purchase, and distribute.

In keeping with these objects, and with others which will become apparent hereinafter, one feature of the present invention resides, briefly stated, in a hemorrhoid inflammation reducing device which has a hollow flexible housing shaped to be inserted into and removed from an anus of a rectum of a person having internal/external hemorrhoids, the housing includes an enlarged head portion to fit into the rectum, a reduced neck portion extending from the head portion so that the neck portion can bear against the internal/external hemorrhoids, and an oversized body portion extending from the neck portion so that the body portion can stick out from the anus allowing the person to grip the body portion for insertion into and removal from the anus of the rectum; a coolant disposed within the housing for shrinking the internal/external hemorrhoids wherein means are provided for sealing the coolant within the housing after the coolant is placed within the housing, the sealing means include a gathering of the housing having an aperture therein formed in distal end of the body portion opposite the neck portion of the housing, and a tie wrapped around the gathering of the housing so that the tie can be tied sealing the coolant in the housing without leaking, and the tie being initially untied allowing the coolant to be initially filled through the aperture contained in the housing when first using the device.

When the hemorrhoid inflammation reducing device is designed in accordance with the present invention, the housing is resilient and deformably shaped so as to be easily inserted and removed from the anus of the rectum of the user, the neck portion bears against the internal/external hemorrhoids, the body portion sticks out from the anus allowing the user to grip the body portion for insertion into and removal from the anus of the rectum, and the sealing means include a tie wrapped around the gathering of the housing allowing the tie to be tied sealing the collant in the housing without leaking.

In accordance with another feature of the present invention, the housing is fabricated out of cold resistant pliable plastic material.

Another feature of the present invention is that the coolant is water frozen into ice.

Yet another feature of the present invention is that the coolant is frozen gel.

In keeping with these objects, and with others which will become apparent hereinafter, another feature of the present invention resides, briefly stated, in a hemorrhoid inflammation reducing device which has a hollow flexible housing shaped to be inserted into and removed from an anus of the rectum of a person having internal-/external hemorrhoids, the housing includes an enlarged head portion to fit into the rectum, a reduced neck portion extending from the head portion so that the neck portion can bear against the internal/external hemorrhoids, and an oversized body portion extending from the neck portion so that the body portion can stick out from the anus allowing the person to grip the body portion for insertion into and removal from the anus of the rectum; a coolant disposed within the housing for shrinking the internal/external hemorrhoids wherein means are provided for sealing the coolant within the housing after the coolant is placed within the housing, the sealing means include a pair of handle-like extensions formed in distal end of the body portion opposite the neck portion of the housing and having a aperture therebetween so that the pair of handle-like extensions can be tied together sealing the coolant in the housing without leaking, and the pair of handle-like extensions being initially untied allowing the coolant to be initially filled through the aperture contained between the handle-like extensions when first using the device.

When the hemorrhoid inflammation reducing device is designed in accordance with the present invention, the reducing device is resilient and deformably shaped so as to be easily inserted and removed from the anus of the rectum of the user, the neck portion bears against the internal/external hemorrhoids, the body portion sticks out from the anus allowing the user to grip the body portion for insertion into and removal from the anus of the rectum, and the sealing means include a pair of handle-like extensions extending from the housing and being tied sealing the coolant in the housing without leaking.

Further objects of the invention will appear as the description proceeds.

To the accomplishment of the above and related objects. This invention may be embodied in the form illustrated in the accompanying drawing, attention being called to the fact, however, that the drawing is illustrative only, and that changes may be made in the specific construction illustrated and described within the scope of the appended claims.

LIST OF REFERENCE NUMERALS UTILIZED IN THE DRAWING

Figure 1:
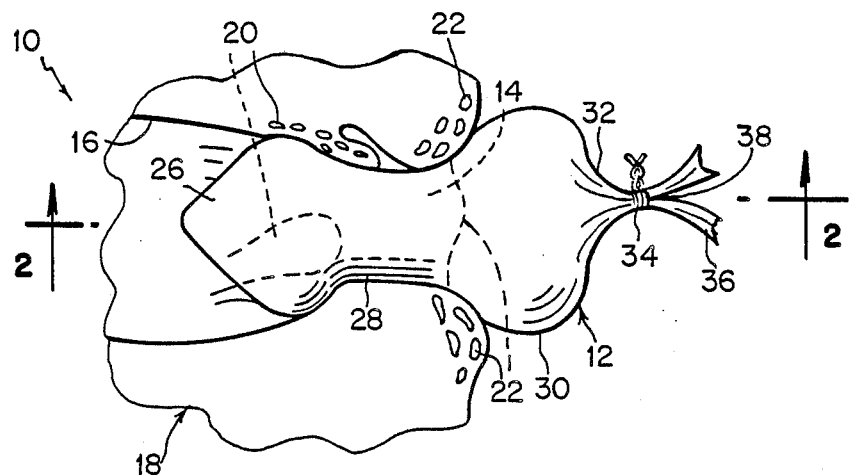
FIG. 1 is a side view of the present invention inserted within the anal canal of a person with hemorrhoids.

10—hemorrhoid inflammation reducing device
12—housing of the hemorrhoid inflammation reducing device 10
14—anus of person 18
16—rectum of person 18
18—person
20—internal hemorrhoids of person 18
22—external hemorrhoids of person 18
24—coolant of the hemorrhoid inflammation reducing device 10

26—head portion of the hemorrhoid inflammation reducing device 10
28—neck portion of the hemorrhoid inflammation reducing device 10
30—body portion of the hemorrhoid inflammation reducing device 10
32—simple closure structure of the hemorrhoid inflammation reducing device 10
33—gathering of closure structure 32
34—tie of the closure structure 32
36—distal end of body portion 30 of the housing 12
38—aperture of the closure structure 32
10'—alternate embodiment of the hemorrhoid inflammation reducing device 10
12'—alternate housing of the alternate closure structure 32'
28'—alternate neck portion of the alternate housing 12'
30'—alternate body of the alternate housing 12'
32'—alternate closure structure
36'—alternate distal end of the alternate closure structure 32'
38'—alternate aperture of the alternate closure structure 32'
46'—handle-like extensions of the alternate closure structure 32'

DETAILED DESCRIPTION OF THE PREFERRED EMBODIMENTS

Turning now descriptively to the drawing, in which similar reference characters denote similar elements throughout the figures.

Figure 2:
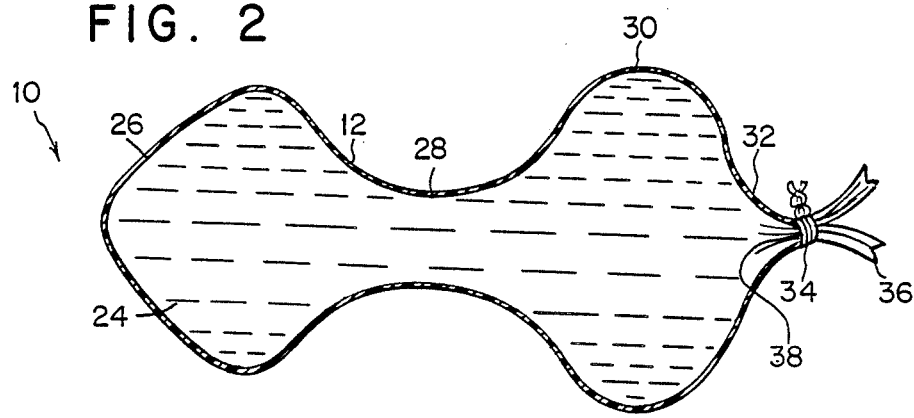
FIG. 2 is a cross sectional view taken along line 2—2 in FIG. 1, showing the internal structure of the present invention.
Figure 3:
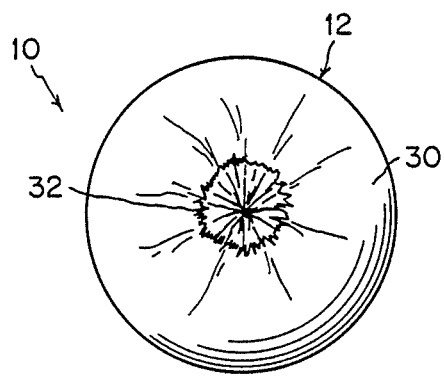
FIG. 3 is an end view of the present invention showing the oversized body portion and closure member.

FIGS. 1, 2, and 3 illustrate a hemorrhoid inflammation reducing device 10. The device 10 consists of a hollow flexible housing 12 shaped to be inserted into and removed from an anus 14 of a rectum 16 of a person 18 having internal hemorrhoids 20 and/or external hemorrhoids 22. A coolant 24 is disposed within the housing 12 for shrinking the internal hemorrhoids 20 and/or the external hemorrhoids 22.

The hollow flexible housing 12 is resilient. To some degree the housing 12 is deformable so that no major discomfort or pain would result from the insertion and removal of the hemorrhoid inflammation reducing device 10 of the present invention.

The housing 12 includes an enlarged head portion 26 to fit into the rectum 16. A reduced neck portion 28 extends from the head portion 26 so that the neck portion 28 can bear against the internal hemorrhoids 20 and/or the external hemorrhoids 22. An oversized body portion 30 extends from the neck poriton 28 so that the body portion 30 can stick out from the anus 14 allowing the person 18 to grip the body portion 30 for insertion into and the removal from the anus 14 of the rectum 16.

The device 10 further includes a simple closure 32 for sealing the coolant 24 within the housing 12 after the coolant 24 is placed within the housing 12. The simple closure structure 32 includes a gathering 33 located in distal end 36 of the body portion 30 opposite the neck portion 28 of the housing 12.

A tie 34 is wrapped around the gathering 33 of the housing 12 and forms a seal that empirically does not leak. The tie 34 seals the coolant 24 therein. The tie 34 can be removed so that the gathering 33 can be opened allowing the coolant 24 to be initially filled through the aperture 38 when first using the device 10. The tie 34 can be a rubber band.

An alternate embodiment of the simple closure 32' for sealing the coolant 24' within the housing 12' after the coolant 24' is placed within the housing 12' follows.

Figure 4:
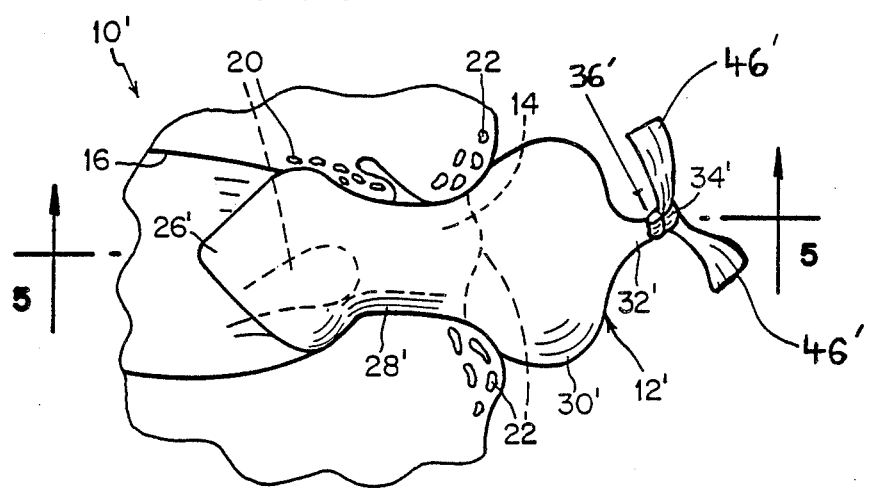
FIG. 4 is a side view of an alternate embodiment of the present invention inserted within the anal canal of a person with hemorrhoids.
Figure 5:
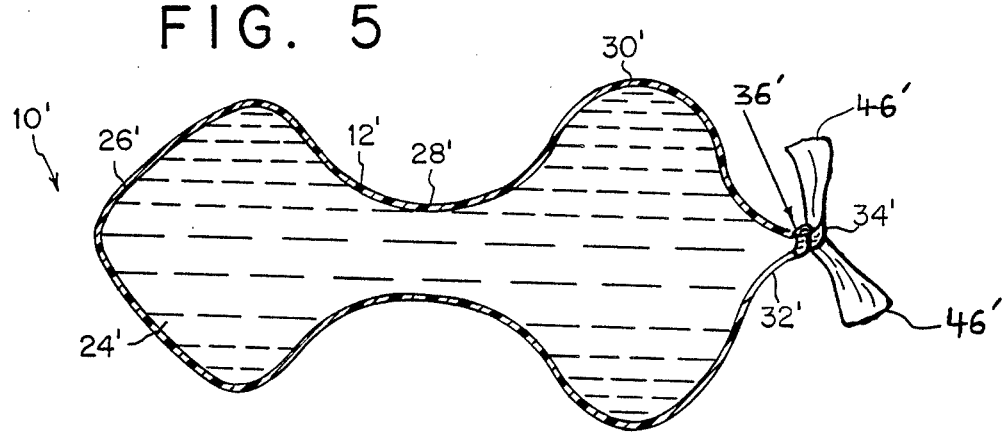
FIG. 5 is a cross sectional view taken along line 5—5 in FIG. 4 showing the internal structure of the alternate embodiment of the present invention.
Figure 6:
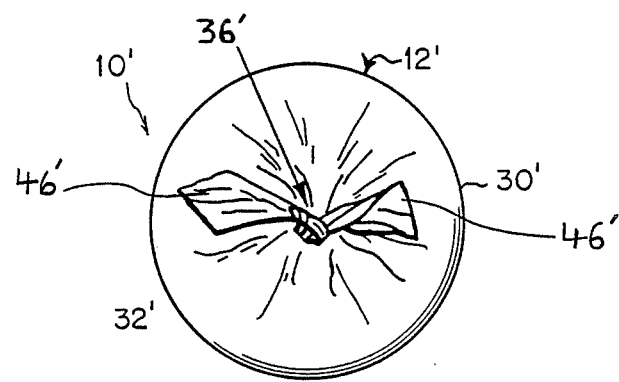
FIG. 6 is an end view of the alternate embodiment of the present invention showing the oversized body portion and closure member.

FIGS. 4, 5, and 6 illustrate the alternate embodiment 10'. The alternate simple closure structure 32' includes a pair of handle-like extensions 46' with aperture 38' therebetween extending from the housing 12' in the vicinity of the distal end 36' of the body 30' opposite the neck portion 28' of the housing 12'.

The handles 46' of the housing 12' form ties that are pulled tightly together; tied and form a seal that empirically does not leak.

The hollow flexible housing 12' is resilient. To some degree the housing 12' is deformable so that no major discomfort or pain would result from the insertion and removal of the hemorrhoid inflammation reducing device 10' of the present invention.

It will be understood that each of the elements described above, or two or more together, may also find a useful application in other types of constructions differing from the type described above.

While the invention has been illustrated and described as embodied in a hemorrhoid inflammation reducing device, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that other can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A hemorrhoid inflammation reducing device, comprising:
   (a) a hollow flexible housing shaped to be inserted into and removed from an anus of a rectum of a person having internal/external hemorrhoids, said housing including an enlarged head portion means to fit into the rectum, a reduced neck poriton means extending from said head portion means so that said neck portion means can bear against the internal/external hemorrhoids, and an oversized body portion means extending from said neck portion means so that said body portion means can stick out from the anus allowing the person to grip said body portion means for inseretion into and removal from the anus of the rectum;
   (b) a coolant means disposed within said housing for shrinking said internal/external hemorrhoids; and
   (c) means for sealing said coolant means within said housing after said coolant means is placed within said housing, said sealing means including a pair of handle-like extension means formed in distal end of said body portion means opposite said neck portion means of said housing and having an aperture therebetween so that said pair of handle-like extension means can be tied together sealing said coolant means in said housing without leaking, and said pair of said handle-like extension means being initially untied for allowing said coolant means to be initially filled through said aperture contained between said handle-like extension means when first using the device.

2. A hemorrhoid inflammation reducing device as defined in claim 1, wherein said housing is fabricated out of cold resistant pliable plastic material.

3. A hemorrhoid inflammation reducing device as defined in claim 1, wherein said coolant means is water frozen into ice.

4. A hemorrhoid inflammation reducing device as defined in claim 1, wherein said coolant means is frozen gel.

* * * * *